(12) United States Patent
Osaka et al.

(10) Patent No.: US 11,369,615 B2
(45) Date of Patent: Jun. 28, 2022

(54) AGENT FOR IMPROVING MITOCHONDRIAL DYSFUNCTION, PREVENTATIVE OR THERAPEUTIC AGENT FOR DISEASES OR SYMPTOMS CAUSED BY MITOCHONDRIAL DYSFUNCTION, AND APPLICATIONS THEREFOR

(71) Applicants: JICHI MEDICAL UNIVERSITY, Tokyo (JP); TOHOKU UNIVERSITY, Miyagi (JP)

(72) Inventors: Hitoshi Osaka, Tochigi (JP); Takanori Yamagata, Tochigi (JP); Eriko Jimbo, Tochigi (JP); Akihiko Miyauchi, Tochigi (JP); Takaaki Abe, Miyagi (JP)

(73) Assignees: JICHI MEDICAL UNIVERSITY, Tokyo (JP); TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/759,486

(22) PCT Filed: Nov. 7, 2018

(86) PCT No.: PCT/JP2018/041354
§ 371 (c)(1),
(2) Date: Apr. 27, 2020

(87) PCT Pub. No.: WO2019/093379
PCT Pub. Date: May 16, 2019

(65) Prior Publication Data
US 2020/0330475 A1    Oct. 22, 2020

(30) Foreign Application Priority Data

Nov. 7, 2017 (JP) .............................. JP2017-214460

(51) Int. Cl.
*A61K 31/407* (2006.01)
*A61K 31/473* (2006.01)
(Continued)

(52) U.S. Cl.
CPC ........ *A61K 31/5415* (2013.01); *A61K 31/407* (2013.01); *A61K 31/473* (2013.01);
(Continued)

(58) Field of Classification Search
CPC ................ A61K 31/407; A61K 31/473; A61K 31/5415; A61K 31/5513; A61K 31/551;
(Continued)

(56) References Cited

U.S. PATENT DOCUMENTS

2004/0248885 A1   12/2004  Auguet et al.
2011/0111011 A1*  5/2011   Giovinazzo .......... A61K 9/2086
                                              424/443
(Continued)

FOREIGN PATENT DOCUMENTS

CA    2920272 A1    8/2016
JP    56166116 A    12/1981
(Continued)

OTHER PUBLICATIONS

Lake et al., Ann. Neurol., publ. 2016, vol. 79, pp. 190-203 (Year: 2016).*

(Continued)

*Primary Examiner* — Sarah Pihonak
(74) *Attorney, Agent, or Firm* — Lucas & Mercanti, LLP

(57) ABSTRACT

A means for substantially improving mitochondrial dysfunction is provided. An aspect of the present invention relates to an agent for improving mitochondrial dysfunction, having a compound represented by the following formula, a stereoisomer or a salt thereof, or a solvate thereof, as an active ingredient. Another aspect of the present invention relates to a medicament or a pharmaceutical composition having the aforementioned compound, a stereoisomer or a pharmaceutically acceptable salt thereof, or a pharmaceutically acceptable solvate thereof, as an active ingredient, for use in preventing or treating a disease or symptom caused by mitochondrial dysfunction.

I-1

I-2

I-3

(Continued)

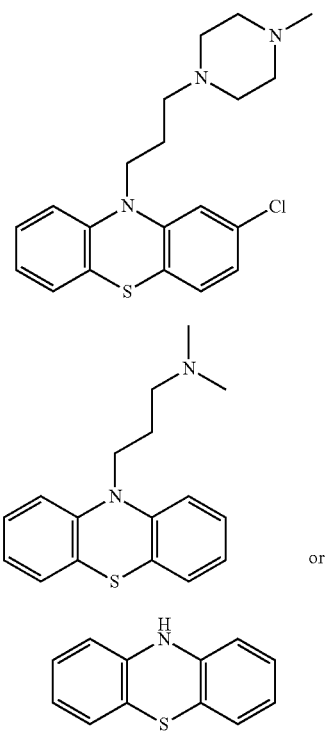

6 Claims, 7 Drawing Sheets

(51) Int. Cl.
| | |
|---|---|
| *A61K 31/5513* | (2006.01) |
| *A61P 25/28* | (2006.01) |
| *A61P 25/00* | (2006.01) |
| *A61P 43/00* | (2006.01) |
| *A61K 31/5415* | (2006.01) |

(52) U.S. Cl.
CPC .......... *A61K 31/5513* (2013.01); *A61P 25/00* (2018.01); *A61P 25/28* (2018.01); *A61P 43/00* (2018.01)

(58) Field of Classification Search
CPC .......... A61P 25/00; A61P 25/28; A61P 27/02; A61P 35/00; A61P 3/10; A61P 3/12; A61P 43/00; A61P 9/10
See application file for complete search history.

(56) References Cited

U.S. PATENT DOCUMENTS

| | | | |
|---|---|---|---|
| 2014/0142095 A1* | 5/2014 | Cortopassi | A61K 31/4453 514/224.8 |
| 2017/0190704 A1* | 7/2017 | Roulet | C07D 471/04 |

FOREIGN PATENT DOCUMENTS

| | | |
|---|---|---|
| JP | 2003506014 A | 2/2003 |
| JP | 2005500337 A | 1/2005 |
| JP | 201241314 A | 3/2012 |
| JP | 2014505095 A | 2/2014 |
| JP | 2014521678 A | 8/2014 |
| JP | 2016514697 A | 5/2016 |
| WO | 0079274 A2 | 12/2000 |
| WO | 2012107706 A1 | 8/2012 |
| WO | 2013017637 A1 | 2/2013 |
| WO | 2014145119 A1 | 9/2014 |

OTHER PUBLICATIONS

El-Hattab et al., Mol. Gen. & Metab., publ. 2015, vol. 116, pp. 4-12 (Year: 2016).*
Khaliulin et al., "Apomorphine prevents myocardial ischemia/reperfusion-induced oxidative stress in the rat heart", Free radical biology & medicine, 2004, vol. 37, No. 7, pp. 969-976.
Shimada et al., "Activation of dopamine D4 receptors is protective against hypoxia/reoxygenation-induced cell death in HT22 cells", Journal of Pharmacological Sciences, 2010, vol. 114, No. 2, pp. 217-224.
Grossini et al.,"Asenapine increases nitric oxide release and protects porcine coronary artery endothelial cells against peroxidation", Vascular Pharmacology, 2014, vol. 60, No. 3, pp. 127-141.
Wang et al.,"Olanzapine and quetiapine protect PC12 cells from B-amyloid peptide 25-35- induced oxidative stress and the ensuing apoptosis", Journal of Neuroscience Research, 2005, vol. 81, No. 4, pp. 572-580.
Stavrovskaya et al., "Clinically approved heterocyclics act on a mitochondrial target and reduce stroke-induced pathology", Journal of Experimental Medicine, 2004, vol. 200, No. 2, pp. 211-222.
Borges et al., "Characterization of hydrophobic interaction and antioxidant properties of the phenothiazine nucleus in mitochondrial and model membranes", Free Radical Research, 2010, vol. 44, No. 9, pp. 1054-1063.
Jung et al., "Apomorphine suppresses TNF-a-induced MMP-9 expression and cell invasion through inhibition of ERK/AP-1 signaling pathway in MCF-7 cells", Biochemical and Biophysical Research Communications, 2017, vol. 487, No. 4, pp. 903-909.
International Search Report for Corresponding International Application No. PCT/JP2018/041354 (3 Pages) (dated Feb. 5, 2019).
Zhelev et al., "Phenothiazines suppress proliferation and induce apoptosis in cultured leukemic ceiis without any influence on the viability of normal lymphocytes", Cancer Chemother Pharmacol, 2004, vol. 53, No. 3, pp. 267-275.
Supplementary European Search Report for Corresponding European Application No. 18876309.8, dated Jul. 16, 2021, 9 Pages.

* cited by examiner

A

B

AGENT FOR IMPROVING MITOCHONDRIAL DYSFUNCTION, PREVENTATIVE OR THERAPEUTIC AGENT FOR DISEASES OR SYMPTOMS CAUSED BY MITOCHONDRIAL DYSFUNCTION, AND APPLICATIONS THEREFOR

CROSS-REFERENCE TO RELATED APPLICATIONS

This application is a 371 of PCT/JP2018/041354, filed Nov. 7, 2018, which claims benefit of Japanese Patent Application No. 2017-214460, filed Nov. 7, 2017.

TECHNICAL FIELD

The present invention relates to an agent for improving mitochondrial dysfunction, a preventive or therapeutic agent for diseases or symptoms caused by mitochondrial dysfunction, and uses of these.

BACKGROUND ART

Mitochondria are organelles of eukaryotic cells mainly responsible for energy generation. Various diseases or symptoms are caused by mitochondrial dysfunction.

Mitochondrial diseases are diseases typically caused by mitochondrial dysfunction. Mitochondrial diseases are hereditary metabolic diseases which occur at a relatively high frequency of 1/500 persons. Mitochondrial diseases may occur in all organs and symptoms remarkably appear particularly in the brain, central nervous system and muscle requiring high energy. Examples of the symptoms in the central nervous system include irreversible intellectual regression, convulsion, stroke-like episode and cerebellar ataxia.

Clinical manifestations of mitochondrial diseases are generally classified into 10 types or more. Of them, Leigh syndrome, and mitochondrial encephalopathy, lactic acidosis and stroke-like episodes (hereinafter also referred to as "MELAS") are regarded as two major clinical manifestations in the field of pediatric medicine. Leigh syndrome causes symptoms such as delayed psychomotor development and regression in the infancy. MELAS interferences with mitochondrial function such as ATP production to cause a symptom such as repetitive stroke-like episode.

For treating diseases or symptoms caused by mitochondrial dysfunction, for example, Patent Literature 1 discloses phenazin-3-one represented by formula (I) and a phenothiazin-3-one derivative compound, or a stereoisomer, a mixture of stereoisomers, a solvate, a hydrate, or a pharmaceutically acceptable salt thereof. The literature discloses that the compound can be used for treating a mitochondrial disorder such as hereditary mitochondrial disease.

Patent Literature 2 discloses a compound selected from a phenothiazine diaminium salt represented by general formula (I) and a pharmaceutically acceptable salt thereof. The literature discloses that the compound and a composition containing the compound can be used for treating mitochondrial diseases. The literature does not disclose pharmacological test results of the compound on treatment of mitochondrial diseases.

Patent Literature 3 discloses use of a thiazole derivative represented by general formula (I) and a compound in the form of a racemic mixture, an enantiomer or any combination of these forms or a pharmaceutically acceptable salt of the compound of general formula (I), for preparing a medicament for treating, e.g., Leigh syndrome or MELAS.

Non Patent Literature 1 discloses that a coenzyme Q10 analog, idebenone, has been approved as a therapeutic agent for Leber's hereditary optic neuropathy, which is a clinical manifestation of a mitochondrial disease, in Europe.

CITATION LIST

Patent Literature

Patent Literature 1: JP Patent Publication (Kohyo) No. 2016-514697
Patent Literature 2: JP Patent Publication (Kohyo) No. 2014-505095
Patent Literature 3: JP Patent Publication (Kohyo) No. 2005-500337

Non Patent Literature

Non Patent Literature 1: Gueven N., Idebenone for Leber's hereditary optic neuropathy, Drugs Today (Barc), Vol. 52 (3), p. 173-181, March, 2016

SUMMARY OF INVENTION

Technical Problem

As described above, it is known that various diseases or symptoms are caused by mitochondrial dysfunction. However, basic therapies for these diseases or symptoms caused by mitochondrial dysfunction have not yet been established. As pharmaceutical agents approved as therapeutic agents for the diseases or symptoms caused by mitochondrial dysfunction, for example, only idebenone (a coenzyme Q10 analog), which is a therapeutic agent for Leber's hereditary optic neuritis, has been known at present in Europe (Non Patent Literature 1). Of the diseases or symptoms caused by mitochondrial dysfunction, particularly, Leigh syndrome and MELAS, which are the two major manifestations in the field of pediatric medicine, had no pharmaceutical agents proved in efficacy for preventing or treating them.

In order to develop a means for preventing or treating the diseases or symptoms caused by mitochondrial dysfunction, it is necessary to find a pharmaceutical agent having an effect to improve mitochondrial dysfunction. However, a pharmaceutical agent having an effect to substantially improve mitochondrial dysfunction has not been known.

In the circumstances, the present invention is directed to providing a means for substantially improving mitochondrial dysfunction.

Solution to Problem

The present inventors conducted various studies on means for solving the aforementioned problems. The present inventors found that a specific compound can substantially improve mitochondrial dysfunction by screening of a known drug library. The present invention was accomplished based on the finding.

More specifically, the present invention will be summarized in the following embodiments.

(1) An agent for improving mitochondrial dysfunction, comprising a compound represented by the following formula:

[Formula 1]

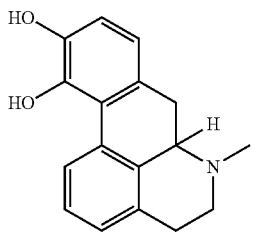
I-1

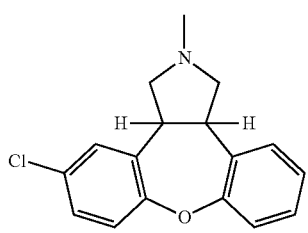
I-2

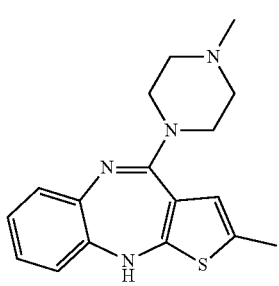
I-3

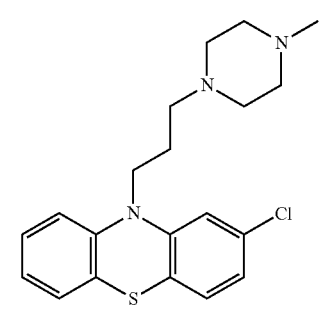
I-4

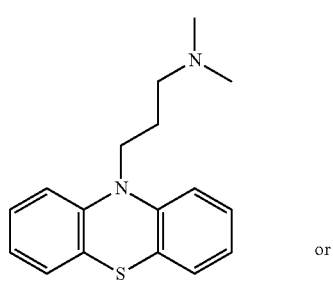
I-5 or

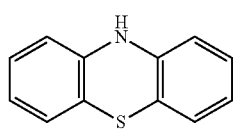
I-6 a stereoisomer or a salt thereof, or a solvate thereof, as an active ingredient.

(2) The agent for improving mitochondrial dysfunction according to embodiment (1), comprising a compound represented by formula (I-1), a stereoisomer or a salt thereof, or a solvate thereof, as an active ingredient.

(3) A medicament for use in preventing or treating a disease or symptom caused by mitochondrial dysfunction, comprising a compound represented by the following formula:

[Formula 2]

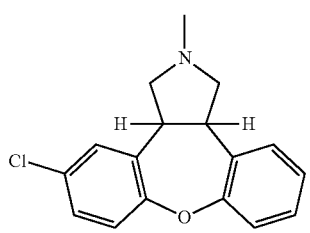
I-1

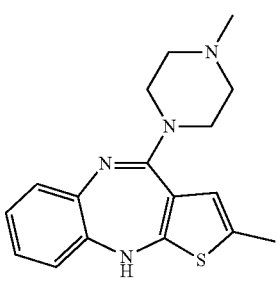
I-2

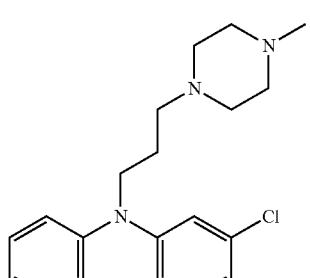
I-3

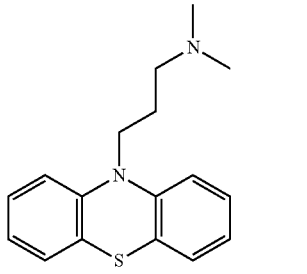
I-4

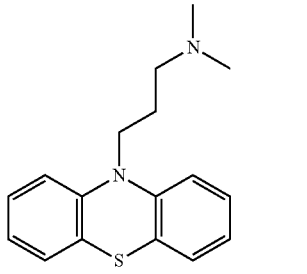
I-5 or

-continued

I-6

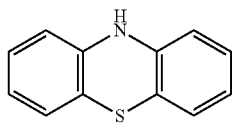

a stereoisomer or a pharmaceutically acceptable salt thereof, or a pharmaceutically acceptable solvate thereof, as an active ingredient.

(4) The medicament according to embodiment (3), comprising a compound represented by formula (I-1), a stereoisomer or a pharmaceutically acceptable salt thereof, or a pharmaceutically acceptable solvate thereof, as an active ingredient.

(5) The medicament according to embodiment (3) or (4), wherein the disease or symptom caused by mitochondrial dysfunction is at least one disease or symptom selected from the group consisting of a mitochondrial disease such as Leigh syndrome, mitochondrial encephalopathy, lactic acidosis and stroke-like episodes (MELAS) or Leber's disease, diabetes and cancer.

(6) A pharmaceutical composition comprising a compound represented by the following formula:

[Formula 3]

I-1

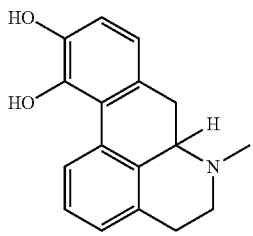

I-2

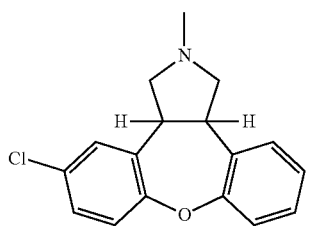

I-3

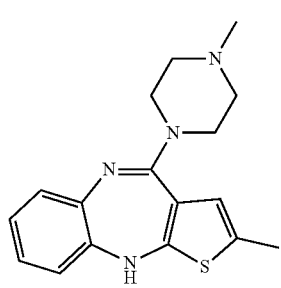

-continued

I-4

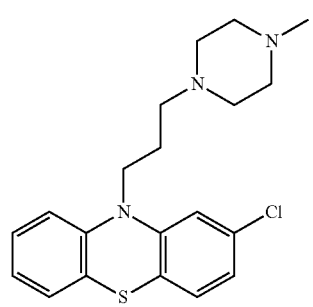

I-5

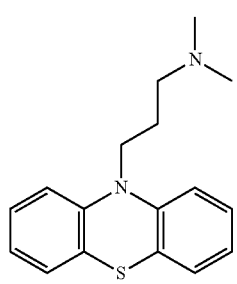

or

I-6

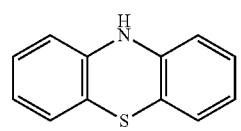

a stereoisomer or a pharmaceutically acceptable salt thereof, or a pharmaceutically acceptable solvate thereof, and at least one pharmaceutically acceptable carrier, for use in preventing or treating a disease or symptom caused by mitochondrial dysfunction.

(7) The pharmaceutical composition according to embodiment (6), comprising a compound represented by formula (I-1), a stereoisomer or a pharmaceutically acceptable salt thereof, or a pharmaceutically acceptable solvate thereof, as an active ingredient.

(8) The pharmaceutical composition according to embodiment (6) or (7), wherein the disease or symptom caused by mitochondrial dysfunction is at least one disease or symptom selected from the group consisting of a mitochondrial disease such as Leigh syndrome, mitochondrial encephalopathy, lactic acidosis and stroke-like episodes (MELAS) or Leber's disease, diabetes and cancer.

Advantageous Effects of Invention

Owing to the present invention, it is possible to provide a means for substantially improving mitochondrial dysfunction.

The objects, constitutions and effects other than the ones mentioned above will be apparent from the description of the following embodiments.

The specification includes the contents described in the specification and/or drawings of JP Patent Application No. 2017-214460 based on which the priority of the present application is claimed.

DESCRIPTION OF EMBODIMENTS

Figure 1:
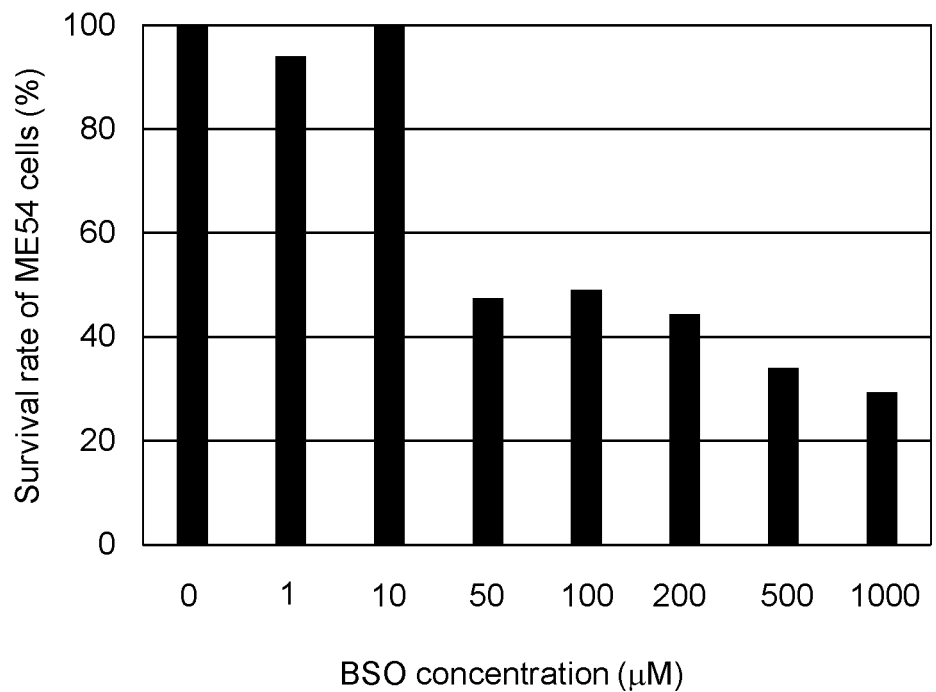
FIG. 1 is a graph showing the relationship between the concentration of L-buthionine-(S,R)-sulfoximine (BSO) added and the survival rate of test cells. A: the results of ME54 cells derived from a patient with Leigh syndrome and B: the results of normal cells, Promol cells.
Figure 1:
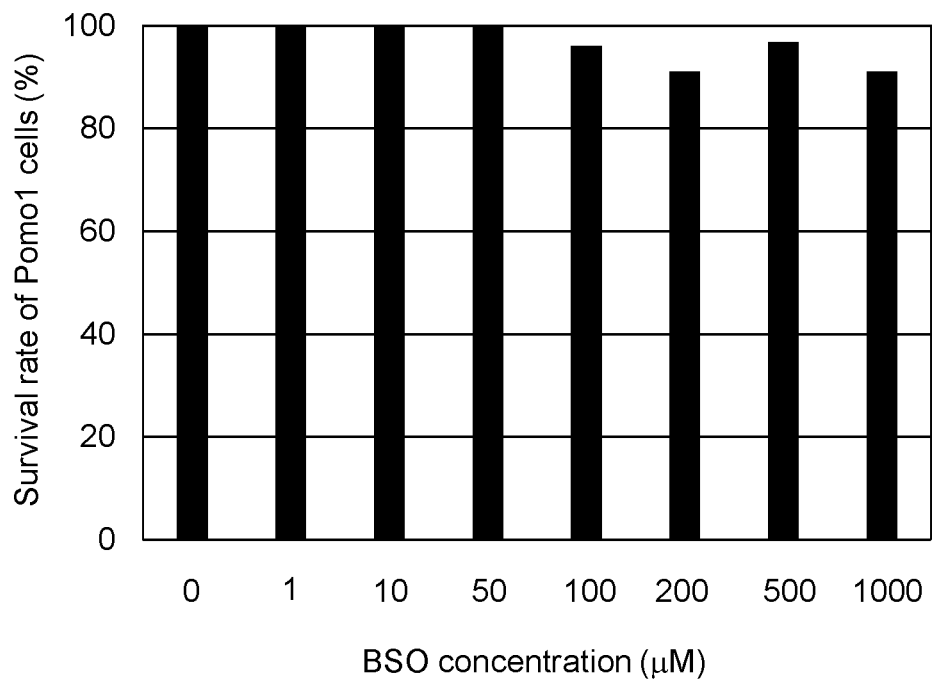

Now, preferable embodiments of the present invention will be more specifically described below.

<1. Agent for Improving Mitochondrial Dysfunction>

In the specification, the "mitochondria" refer to small organelles in eukaryotic cells, responsible for energy generation. As the disease or symptom caused by mitochondrial dysfunction, various diseases or symptoms are known. However, basic therapies for these diseases or symptoms caused by mitochondrial dysfunction have not yet been established. Of the diseases or symptoms caused by mitochondrial dysfunction, particularly, Leigh syndrome and MELAS, which are two major manifestations in the field of pediatric medicine, had no pharmaceutical agents proved in efficacy for preventing or treating them.

In order to develop a means for preventing or treating a disease or symptom caused by mitochondrial dysfunction, it is necessary to find a pharmaceutical agent having an effect to improve mitochondrial dysfunction. Particularly, a pharmaceutical agent producing a desired prevention or therapeutic effect on a disease or symptom, such as Leigh syndrome and MELAS, a main manifestation of which appears in the brain or central nervous system, is preferably considered to have a pharmacokinetic property of passing through the blood-brain barrier to reach the brain or central nervous system. However, a pharmaceutical agent having the aforementioned effect and property has not been known.

The present inventors found that a specific compound expectedly reaching the brain or central nervous system can substantially improve mitochondrial dysfunction by screening a known drug library. Accordingly, an aspect of the present invention relates to an agent for improving mitochondrial dysfunction, comprising a compound represented by the following formula:

[Formula 4]

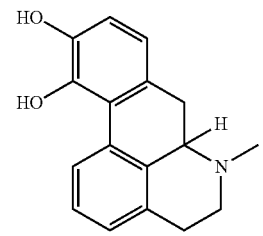

I-1

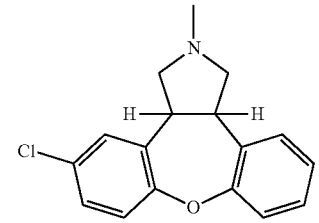

I-2

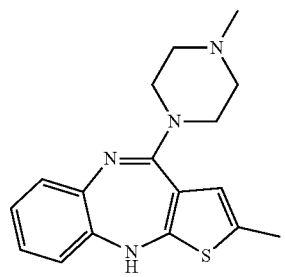

I-3

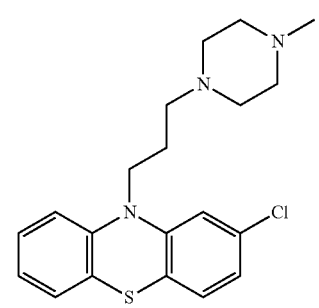

I-4

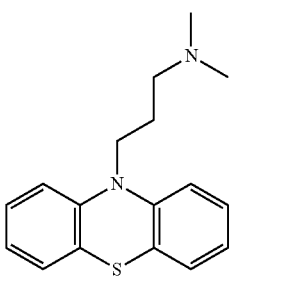

I-5 or

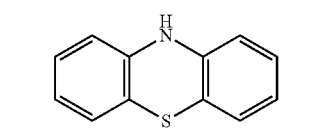

I-6 a stereoisomer or a salt thereof, or a solvate thereof, as an active ingredient. The compound represented by the above formula, a stereoisomer or a salt thereof, or a solvate thereof is known to pass through the blood-brain barrier. Because of this, these compounds can be delivered to the brain or central nervous system and improve mitochondrial dysfunction, with the result that various diseases or symptoms caused by mitochondrial dysfunction can be prevented and treated.

In the aspects of the present invention, mitochondria refer to the ones generally present in cells of eukaryotes, for example, a human or a non-human mammal (for example, warm-blooded animal such as pig, dog, cow, rat, mouse, guinea pig, rabbit, chicken, sheep, cat, monkey, baboon or chimpanzee) or a cell structure thereof, and particularly the ones present in cells of a human or a cell structure thereof. The function of mitochondria present in the cells of the aforementioned organisms or a cell structure thereof can be substantially improved by administering, e.g., a compound represented by any one of the above formulae or a medicament comprising the compound as an active ingredient to the cells or a cell structure thereof.

In the aspects of the present invention, mitochondrial dysfunction generally refers to the state where at least one mitochondrial function, which is selected from the group consisting of oxygen respiration, ATP production, and metabolism of fat, sugar, amino acid or uric acid, is substantially low compared to the function in the normal state.

In the aspects of the present invention, the mitochondrial dysfunction improvement effect of the compound to be used as an active ingredient can be determined, for example, by the following means but the means are not limited to the followings. When mitochondria become dysfunctional, for example, ATP production is damaged and/or an oxidative stress increases, with the result that apoptosis of cells is induced. Because of this, an individual having mitochondrial dysfunction is reported to be less tolerant to oxidative stress, compared to a normal individual (Shrader W D et al., Bioorg Med Chem Lett., Jun. 15, 2011, Vol. 21 (12), p. 3693-8, doi: 10.1016/j.bmcl.2011.04.085. electronically published on Apr. 24, 2011, PubMed PMID: 21600768). Then, oxidative stress (for example, addition of L-buthionine-(S,R)-sulfoximine (hereinafter referred also to as "BSO")) is given to cells (for example, skin fibroblasts) of a subject having a disease or symptom caused by mitochondrial dysfunction to induce apoptosis. Under the conditions, a test compound is added to the cells. After culturing for a predetermined period, the survival rate of the cells to which the test compound was added is compared to that of the control cells. In this manner, improvement of the survival rate is confirmed and the improvement effect of mitochondrial dysfunction can be evaluated. Alternatively, a test compound is added to the cells (for example, skin fibroblasts) of a subject having a disease or symptom caused by mitochondrial dysfunction, and thereafter, the oxygen consumption rate (hereinafter referred also to as "OCR") of mitochondria during ATP synthesis in the cells is continuously measured by use of an extracellular flux analyzer while ATP synthase inhibitors (for example, oligomycin and rotenone) and an uncoupler (for example, carbonyl cyanide-p-trifluoromethoxy phenylhydrazone (FCCP)) are added. In this manner, mitochondrial function can be evaluated. Examples of the evaluation items to be analyzed include basal respiratory volume, ATP production (capacity) and maximum respiratory volume, which are major indexes for evaluating mitochondrial function. Based on these evaluation items, the improvement effect of mitochondrial dysfunction can be evaluated.

In the aspects of the present invention, a compound represented by any one of the above formulae and used as an active ingredient can produce the improvement effect of mitochondrial dysfunction, which is determined in accordance with the aforementioned procedure, usually in an amount of 10 nM or more, for example, within the range of 10 nM to 10 μM, preferably 10 nM to 1 μM, and particularly 10 to 100 nM.

Examples of the compounds represented by the above formulae, a stereoisomer or a salt thereof, or a solvate thereof include pharmaceutical agents known as active ingredients of pharmaceutical products. Examples of the compound represented by formula (I-1) include R(−)-apomorphine hydrochloride hemihydrate (pharmaceutical agent No. 5, formula (I-1-1)), which is known as a Parkinson's disease therapeutic agent; examples of the compound represented by formula (I-2) include asenapine maleate (pharmaceutical agent No. 105, formula (I-2-1)), which is known as a schizophrenia therapeutic agent; examples of the compound represented by formula (I-3) include olanzapine (pharmaceutical agent No. 118, formula (I-3-1)), which is known as an atypical antipsychotic; examples of the compound represented by formula (I-4) include prochlorperazine dimaleate (pharmaceutical agent No. 35, formula (I-4-1)), which is known as a schizophrenia therapeutic agent; examples of the compound represented by formula (I-5) include promazine hydrochloride (pharmaceutical agent No. 56, formula (I-5-1)), which is known as a tranquilizer; and examples of the compound represented by formula (I-6) include phenothiazine (pharmaceutical agent No. 129, formula (I-6-1)), which is known as a tranquilizer. These compounds can be provided by those skilled in the art by purchasing or preparing them by themselves based on the common names and the following chemical structures.

[Formula 5]

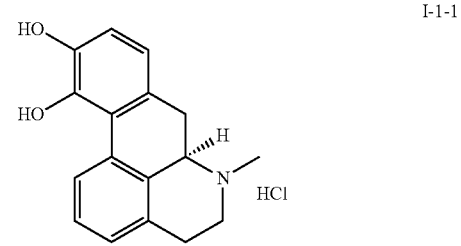

I-1-1

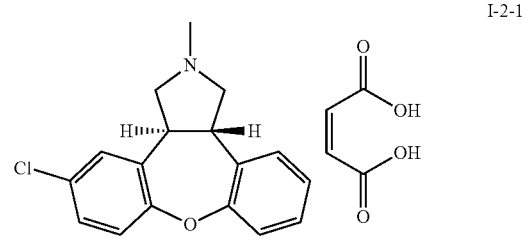

I-2-1

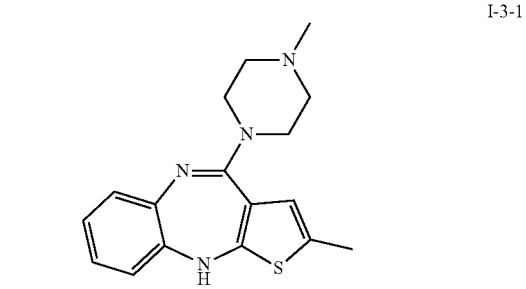

I-3-1

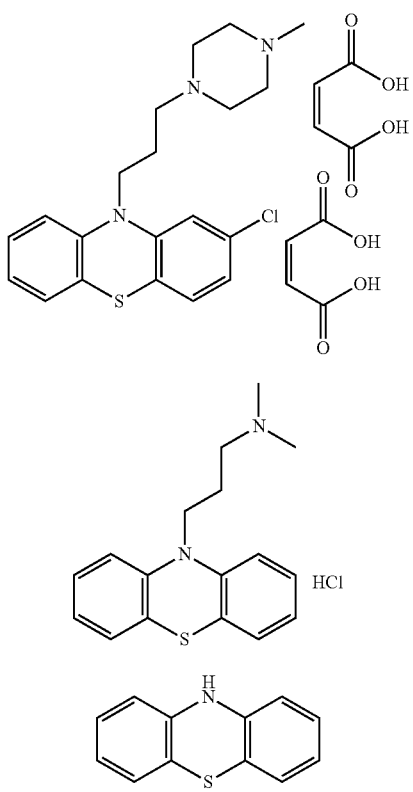

I-4-1

I-5-1

I-6-1

In the aspects of the present invention, the compound to be used as an active ingredient is preferably a compound represented by formula (I-1-1), (I-2-1), (I-3-1), (I-4-1), (I-5-1) or (I-6-1). The mitochondrial dysfunction can be strongly improved by using any one of these compounds having aforementioned features, as an active ingredient.

In the aspects of the present invention, the compound to be used as an active ingredient is preferably a compound represented by formula (I-1) and particularly preferably a compound represented by formula (I-1-1). The mitochondrial dysfunction can be particularly strongly improved by using a compound represented by the above formula as an active ingredient.

In the aspects of the present invention, the compounds represented by formulae (I-1), (I-2), (I-3), (I-4), (I-5) and (I-6), and particularly the compounds represented by formulae (I-1-1), (I-2-1), (I-3-1), (I-4-1), (I-5-1) and (I-6-1) each include not only the compound itself but also a salt thereof. As the salts of the compounds represented by the above formulae, which are not limited, a salt with a cation such as a sodium ion, a potassium ion, a calcium ion, a magnesium ion, or a substituted or unsubstituted ammonium ion; an inorganic acid such as hydrochloric acid, hydrobromic acid, sulfuric acid, nitric acid, carbonic acid or phosphoric acid; or a salt with an organic acid anion such as formic acid, acetic acid, maleic acid, fumaric acid, benzoic acid, ascorbic acid, lactic acid, succinic acid, bismethylene salicylic acid, methanesulfonic acid, ethanedisulfonic acid, propionic acid, tartaric acid, malic acid, salicylic acid, citric acid, gluconic acid, aspartic acid, stearic acid, palmitic acid, itaconic acid, glycolic acid, p-aminobenzoic acid, glutamic acid, benzenesulfonic acid, cyclohexylsulfamic acid, methanesulfonic acid, ethanesulfonic acid, isethionic acid, p-toluenesulfonic acid or naphthalene sulfonic acid is preferable.

If each of the compounds represented by the above formulae is in the form of a salt, the compound can be used without substantially reducing the improvement effect of mitochondrial dysfunction.

In the aspects of the present invention, the compounds represented by formulae (I-1), (I-2), (I-3), (I-4), (I-5) and (I-6), particularly the compounds represented by formulae (I-1-1), (I-2-1), (I-3-1), (I-4-1), (I-5-1) and (I-6-1) each include not only the compound itself but also a solvate of the compound or a salt thereof. As a solvent that can form a solvate with each of the compounds represented by the above formulae or a salt thereof, which is not limited, for example, water or an organic solvent including a lower alcohol (an alcohol having 1 to 6 carbon atoms such as methanol, ethanol or 2-propanol (isopropyl alcohol)) and a higher alcohol (an alcohol having 7 or more carbon atoms such as 1-heptanol or 1-octanol), dimethyl sulfoxide (DMSO), acetic acid, ethanolamine or ethyl acetate is preferable. If each of the compounds represented by the above formulae or a salt thereof is in the form of a solvate with the above solvent, the compound can be used without substantially reducing the improvement effect of mitochondrial dysfunction.

In the aspects of the present invention, the compounds represented by formulae (I-1), (I-2), (I-3), (I-4), (I-5) and (I-6), particularly the compounds represented by formulae (I-1-1), (I-2-1), (I-3-1), (I-4-1), (I-5-1) and (I-6-1) each include not only the compound itself but also the protected form thereof. In the specification, the "protected form" refers to the form obtained by introducing a protecting group(s) into a single or a plurality of functional groups (for example, a hydroxyl group or an amino group). In the specification, the protected form of the compound sometimes is referred to as a protected derivative of the compound. In the specification, the "protecting group" refers to a group, which is introduced into a predetermined functional group in order to prevent progression of an undesirable reaction, and quantitatively removed under predetermined reaction conditions, and substantially stable, i.e., inactive in reactions, under the reaction conditions other than the predetermined conditions. The protecting group that can form a protected form of the compound is not limited. For example, as the protecting group for a hydroxyl group, silyl (for example, t-butyryl dimethyl silyl (TBS), triisopropylsilyl (TIPS) or tert-butyl diphenylyl silyl (TBDPS)) or alkoxy (for example, methoxymethoxy (MOM) or methoxy (Me)) is preferable. As the protecting group for an amino group, t-butoxycarbonyl (Boc), 2-bromobenzyloxycarbonyl (BrZ) or 9-fluorenylmethoxycarbonyl (Fmoc) is preferable. The protection with the protecting group and the deprotection can be appropriately carried out by those skilled in the art based on the reaction conditions ordinarily known. If each of the compounds represented by the above formulae is the protected form with the above protecting group, the compound can be used without substantially reducing the improvement effect of mitochondrial dysfunction.

In the aspects of the present invention, if each of the compounds represented by formulae (I-1), (I-2), (I-3), (I-4), (I-5) and (I-6), particularly each of the compounds represented by formulae (I-1-1), (I-2-1), (I-3-1), (I-4-1), (I-5-1) and (I-6-1) has a single or a plurality of tautomers, the compound also includes the form of individual tautomers of the compound.

In the aspects of the present invention, if each of the compounds represented by formulae (I-1), (I-2), (I-3), (I-4), (I-5) and (I-6), particularly each of the compounds represented by formulae (I-1-1), (I-2-1), (I-3-1), (I-4-1), (I-5-1)

and (I-6-1) has a single or a plurality of stereogenic centers (chiral centers), the compound also includes stereoisomers of the compound, including enantiomers and diastereomers of the compound and a mixture thereof such as a racemate.

Since the compounds represented by formulae (I-1), (I-2), (I-3), (I-4), (I-5) and (I-6), particularly the compounds represented by formulae (I-1-1), (I-2-1), (I-3-1), (I-4-1), (I-5-1) and (I-6-1) have the aforementioned features, they can exert an effect to highly improve mitochondrial dysfunction.

<2. Pharmaceutical Use>

As previously described, if a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) is administered to eukaryotic cells (examples thereof are given above) or a cell structure thereof, mitochondrial dysfunction in the cells or a cell structure thereof can be substantially improved. Accordingly, another aspect of the present invention relates to a medicament comprising a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient, for use in improving mitochondrial dysfunction.

The compound represented by any one of formulae (I-1), (I-2), (I-3), (I-4), (I-5) and (I-6), particularly the compound represented by any one of formulae (I-1-1), (I-2-1), (I-3-1), (I-4-1), (I-5-1) and (I-6-1) is a pharmaceutical agent known as an active ingredient of a pharmaceutical product or includes such a pharmaceutical agent known in the art. These pharmaceutical agents known as active ingredients of pharmaceutical products have been sufficiently confirmed in safeness. Accordingly, each of the compounds represented by the above formulae can be applied to various pharmaceutical uses of the present invention as an active ingredient confirmed in safeness.

The compounds represented by formulae (I-1), (I-2), (I-3), (I-4), (I-5) and (I-6), particularly the compounds represented by formulae (I-1-1), (I-2-1), (I-3-1), (I-4-1), (I-5-1) and (I-6-1) are known to be able to pass through the blood-brain barrier. Accordingly, each of the compounds represented by the above formulae is delivered to the brain or central nervous system and improves mitochondrial dysfunction, with the result that various diseases or symptoms caused by mitochondrial dysfunction can be prevented or treated.

If a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) is applied to pharmaceutical use, the compound includes not only the compound itself but also a stereoisomer of the compound, a pharmaceutically acceptable salt thereof, and a pharmaceutically acceptable solvate thereof. As each of the compounds represented by the above formulae, and a pharmaceutically acceptable salt of a stereoisomer thereof, and a pharmaceutically acceptable solvate thereof, which are not limited, for example, a salt or solvate thereof (examples thereof are given above) is preferable. If each of the compounds represented by the above formulae or a stereoisomer thereof is in the form of a salt or solvate, the compound can be applied to desired pharmaceutical use without substantially reducing the improvement effect of mitochondrial dysfunction.

If a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) is applied to pharmaceutical use, the compound includes not only the compound itself but also the form of a prodrug of the compound. In the specification, the "prodrug" refers to a compound, which is converted into a parent drug in vivo. The forms of a prodrug of the compound, which are not limited, are as follows. For example, if a hydroxyl group is present, an ester of the hydroxyl group with a carboxylic acid, and an amide of the hydroxyl group with an amine can be mentioned. For example, if an amino group is present, an amide of the amino group with a carboxylic acid can be mentioned. If each of the compounds represented by the above formulae is in the form of a prodrug, pharmacokinetics at the time of administration of the form of a prodrug to a subject can be improved without substantially reducing the improvement effect of the compounds represented by the above formulae serving as a parent drug on mitochondrial dysfunction.

If a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) is applied to pharmaceutical use, the compound may be used alone or in combination with at least one pharmaceutically acceptable component. The medicament of the present aspect can be prepared into various dosage forms ordinarily used in the technical field depending on a desired administration method. Accordingly, the medicament of the present aspect may be provided in the form of a pharmaceutical composition comprising a compound represented by any one of the above formulae, a stereoisomer or a salt thereof, or a solvate thereof, and at least one pharmaceutically acceptable carrier. The pharmaceutical composition of the present aspect may comprise, in addition to the aforementioned components, e.g., at least one pharmaceutically acceptable medium (for example, a solvent such as sterile water or a solution such as saline), an excipient, a binder, a vehicle, a solubilization agent, a preservative, a stabilizer, a puffing agent, a lubricant, a surfactant, an emulsifier, an oily liquid (for example, vegetable oil), a suspension agent, a buffer, a soothing agent, an antioxidant, a sweetener and a flavoring agent.

The medicament of the present aspect, which comprises a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient, which is not particularly limited in dosage form, may be a formulation for use in parenteral administration or oral administration. The dosage form of the medicament of the present aspect may be a single unit-dose formulation or a multiple-dose formulation. Examples of the formulation for use in parenteral administration include injections such as an aseptic solution or a suspension prepared by using water or a pharmaceutically acceptable medium other than water, lotions, ointments, eye drops and suppositories. Examples of a component that can be blended with injections include, but are not limited to, a vehicle such as an isotonic solution containing saline, glucose or another adjuvant (for example, D-sorbitol, D-mannitol, D-mannose or sodium chloride); a solubilization agent such as an alcohol (for example, ethanol or benzyl alcohol), a polyalcohol (for example, propylene glycol or polyethylene glycol) or an ester (for example, benzyl benzoate); a nonionic surfactant such as polysorbate 80 (trademark) or polyoxyethylene hydrogenated castor oil; an oily liquid such as sesame oil or soybean oil; a buffer such as a phosphate buffer or a sodium acetate buffer; a soothing agent such as benzalkonium chloride or procaine hydrochloride; a stabilizer such as human serum albumin or polyethylene glycol; a preservative; and an antioxidant. The injection prepared is usually put in appropriate vials (for example, ampoule) and stored in an appropriate environment until use.

Examples of the formulation for use in oral administration include a tablet, a pill, a powder dispensing, a granule, a powder, a capsule, a microcapsule, an elixir, a liquid, a syrup, a slurry agent and a suspension. The tablet may have a dosage form such as a sugar-coated tablet, which is prepared by applying sugar coating or soluble coating, a gelatin encapsulated tablet, an enteric coated tablet or a film coated tablet, if desired; or a dosage form such as a double-layered tablet or a multi-layered tablet.

Examples of a component to be blended with, e.g., a tablet or a capsule include, but are not limited to, a binder such as water, ethanol, propanol, single syrup, a glucose solution, carboxymethyl cellulose, shellac, methyl cellulose, potassium phosphate, polyvinylpyrrolidone, gelatin, cornstarch, tragacanth gum or gum Arabic; an excipient such as crystalline cellulose, lactose, white sugar, sodium chloride, glucose, urea, starch, calcium carbonate, kaolin or silicic acid; a disintegrant such as dried starch, sodium alginate, agar powder, laminaran powder, sodium hydrogen carbonate, calcium carbonate, polyoxyethylene sorbitan fatty acid ester, sodium lauryl sulfate, stearic acid monoglyceride, starch or lactose; a disintegration inhibitor such as white sugar, stearin cocoa butter or hydrogenated oil; an absorption promoter such as a quaternary ammonium salt or sodium lauryl sulfate; a moisturizer such as glycerin or starch; an adsorbent such as starch, lactose, kaolin, bentonite or colloidal silicic acid; a lubricant such as purified talc, stearate (for example, magnesium stearate), boric acid powder or polyethylene glycol; a sweetener such as sucrose, lactose or saccharin; and a flavoring agent such as peppermint, *Gaultheria adenothrix* oil or cherry. If a formulation is a capsule, a liquid carrier such as a fat and oil may be further contained.

The medicament of the present aspect can be formulated as a depot formulation. In this case, the medicament of the present aspect in the dosage form of a depot formulation can be embedded under the skin or muscle or administered intramuscularly by injection. By applying the medicament of the present aspect to a depot formulation, the mitochondrial dysfunction improvement effect of a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) can be sustained over a long time period.

The medicament of the present aspect, which comprises a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient, can be used in combination with one or more additional pharmaceutical agents useful as a medicament. In the medicament of the present aspect, examples of the additional pharmaceutical agents to be used in combination with the compound represented by any one of the above formulae include, but are not limited to, at least one of the compounds represented by the aforementioned formulae excluding the above compound, such as idebenone, taurine, 5-aminolevulinic acid (5-ALA) and vatiquinone (EPI-743). In this case, the form of the medicament of the present aspect is a combined medicine comprising a compound represented by any one of the above formulae, a stereoisomer or a pharmaceutically acceptable salt thereof, or a pharmaceutically acceptable solvate thereof and one or more additional pharmaceutical agents. The combined medicine may be in the form of a pharmaceutical composition comprising a compound represented by any one of the above formulae, a stereoisomer or a pharmaceutically acceptable salt thereof, or a pharmaceutically acceptable solvate thereof and one or more additional pharmaceutical agents in combination, or may be in the form of a pharmaceutical composition comprising a compound represented by any one of the above formulae, a stereoisomer or a pharmaceutically acceptable salt thereof, or a pharmaceutically acceptable solvate thereof, which is used in combination with one or more additional pharmaceutical agents. If the medicament of the present aspect is in the form of a combined medicine as mentioned above, the combined medicine may be provided in a form of a single formulation comprising a compound represented by any one of the above formulae, a stereoisomer or a pharmaceutically acceptable salt thereof, or a pharmaceutically acceptable solvate thereof and one or more additional pharmaceutical agents; or may be provided in a form of a pharmaceutical combination or a kit comprising a plurality of formulations separately formulated from the compound and one or more additional pharmaceutical agents. In the case of being in a form of a pharmaceutical combination or a kit, individual formulations can be simultaneously or separately (for example, successively) administered.

The medicament of the present aspect, which comprises a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient, can also prevent or treat various diseases, symptoms and/or disorders caused by mitochondrial dysfunction. Examples of the diseases, symptoms and/or disorders include, but are not limited to, mitochondrial diseases such as Leigh syndrome, mitochondrial encephalopathy, lactic acidosis and stroke-like episodes (MELAS) or Leber's disease, diabetes and cancer. By administering the medicament of the present aspect to a subject which requires prevention or treatment for the disease, symptom or disorder, at least one disease or symptom, which is selected from the group consisting of the diseases, symptoms or disorders caused by mitochondrial dysfunction, for example, a mitochondrial disease such as Leigh syndrome, MELAS or Leber's disease, diabetes and cancer, can be prevented or treated.

The medicament of the present aspect, which comprises a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient, can be applied to various subjects, which require prevention or treatment for the disease, symptom or disorder caused by mitochondrial dysfunction. The subject is usually preferably a eukaryote, for example, a test subject or a patient, more specifically, a human or a non-human mammal (for example, warm-blooded animal such as pig, dog, cow, rat, mouse, guinea pig, rabbit, chicken, sheep, cat, monkey, baboon or chimpanzee). By administering the medicament of the present aspect to a subject as mentioned above, the disease, symptom and/or disorder of the subject, caused by mitochondrial dysfunction can be prevented or treated.

In the specification, the "prevention" refers to substantially preventing occurrence (development or manifestation) of a symptom, disease and/or disorder. In the specification, the "treatment" refers to suppressing (for example, suppression of progression), mitigating, recovering and/or curing a symptom, disease and/or disorder that occurs (develops or manifests).

A compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) can be used in a subject having the aforementioned symptom, disease and/or disorder (for example, mitochondrial disease, diabetes or cancer) for preventing or treating the symptom, disease and/or disorder. Accordingly, the medicament of the present aspect is preferably a medicament for use in preventing or treating the aforementioned symptom, disease and/or disorder (for example, mitochondrial disease, diabetes or cancer), and more preferably, a medicament for use in preventing or treating at least one disease or symptom selected from the group consisting of a mitochondrial disease such as Leigh syndrome, MELAS or Leber's disease, diabetes and cancer. By using the medicament of the present aspect for preventing or treating the symptom, disease and/or disorder caused by mitochondrial dysfunction, the symptom, disease and/or disorder can be prevented or treated through the mitochondrial dysfunction improvement effect of the compound represented by any one of the above formulae.

A compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1) can be used in a subject having a symptom, the aforementioned disease and/or disorder (for example, mitochondrial disease, diabetes or cancer) for preventing or treating the symptom, disease and/or disorder. Accordingly, another aspect of the present invention relates to a method for preventing or treating a disease or symptom caused by mitochondrial dysfunction, comprising administering an effective amount of a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof to a subject which requires prevention or treatment of the aforementioned symptom, disease and/or disorder (for example, mitochondrial disease, diabetes or cancer). The symptom, disease and/or disorder is preferably at least one disease or symptom selected from the group consisting of a mitochondrial disease such as Leigh syndrome, MELAS or Leber's disease, diabetes and cancer. By administering a compound represented by any one of the above formulae to a subject which requires prevention or treatment of the symptom, disease and/or disorder caused by mitochondrial dysfunction, the symptom, disease and/or disorder can be prevented or treated through mitochondrial dysfunction improvement effect of the compound represented by any one of the above formulae.

Another aspect of the present invention is a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof for use in preventing or treating the aforementioned symptom, disease and/or disorder (for example, mitochondrial disease, diabetes or cancer). Another aspect of the present invention is use of a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof in the manufacture of a medicament for preventing or treating the aforementioned symptom, disease and/or disorder (for example, mitochondrial disease, diabetes or cancer). The symptom, disease and/or disorder is preferably at least one disease or symptom selected from the group consisting of a mitochondrial disease such as Leigh syndrome, MELAS or Leber's disease, diabetes and cancer. By using a compound represented by any one of the above formulae or the medicament of the present aspect for preventing or treating the symptom, disease and/or disorder caused by mitochondrial dysfunction, the symptom, disease and/or disorder can be prevented or treated through mitochondrial dysfunction improvement effect of the compound represented by any one of the above formulae.

When a medicament comprising a compound represented by formula (I-1), (I-2), (I-3), (I-4), (I-5) or (I-6), particularly a compound represented by formula (I-1-1), (I-2-1), (I-3-1), (I-4-1), (I-5-1) or (I-6-1), a stereoisomer or a pharmaceutically acceptable salt thereof, or a pharmaceutically acceptable solvate thereof, as an active ingredient is administered to a subject, particularly a human patient, the accurate dose and usage (for example, dosage, the number of administration times and/or route of administration) should be eventually determined by a doctor in charge in consideration of various factors such as the age and sex of a subject, the accurate conditions (for example, severity) of the symptom, disease and/or disorder to be prevented or treated, and the route of administration and in view of a therapeutically effective dosage, the number of administration times and route of administration. Accordingly, a compound represented by any one of the above formulae and serving as an active ingredient in the medicament of the present aspect is administered to a subject in a therapeutically effective amount and at the number of times. For example, if the medicament of the present aspect is administered to a human patient, the dosage of a compound represented by any one of the above formulae and serving as an active ingredient usually falls within the range of 0.001 to 100 mg/kg body weight per dose, typically 0.01 to 10 mg/kg body weight per dose, and particularly 0.1 to 10 mg/kg body per dose. The number of administration times of the medicament of the present aspect is, for example, one or a plurality of times (for example, 2 or 3 times) per day or once at intervals of several days. The administration route of the medicament of the present aspect is not particularly limited. The medicament may be orally or parenterally (for example, intrarectally, intramucosally, intestinally, intramuscularly, subcutaneously, intramedullary, intrathecally, direct-intraventricularly, intravenously, intravitreally, intraperitoneally, intranasally or intraocularly) administered once or a plurality of times. By using the medicament of the present aspect in the aforementioned dose and usage, the symptom, disease and/or disorder caused by mitochondrial dysfunction can be prevented or treated through mitochondrial dysfunction improvement effect of a compound represented by any one of the above formulae.

EXAMPLES

Now, the present invention will be more specifically described by way of Examples; however, the technical scope of the present invention is not limited to these Examples.

<I. Materials>

[I-1. Compound]

Of the diseases or symptoms caused by mitochondrial dysfunction, Leigh syndrome, MELAS or the like is a disease whose symptom mainly occurs in the central nervous system. Then, a library of commercially available drugs (Prestwick the Chemical Library, Ver.16; central nervous system agonist, Prestwick Chemical, Inc.), which are known to pass through the blood-brain barrier, was used. The drug library contains 137 known pharmaceutical agents.

[I-2. Cells]

In the experiment shown below, skin fibroblasts, which were separately established from patients having Leigh syndrome caused by nuclear gene mutation, patients having Leigh syndrome caused by mitochondrial gene mutation, or patients having MELAS, were used. The gene mutations in the patients having Leigh syndrome are all mutations decreasing the activity of respiratory chain complex I. As normal cells used as a control, normal skin fibroblasts purchased from PromoCell GmbH were used. The samples were previously approved in the ethics committee of Jichi Medical University Hospital and all patients' families gave informed consent.

TABLE 1

| Cell ID | Disease | Age | Gene mutation | Protein | Mutation rate (%) |
|---|---|---|---|---|---|
| KCMC10 | Leigh syndrome | 0 | m.10158T > C | ND3 | 90 |
| ME54 | Leigh syndrome | 5 | c.55C > T, p(P19S) | NDUFA1 | — |
| ME110 | MELAS | 14 | m.3242A > G | (tRNA-Leu) | 21 |
| Promo1 | Normal (Control) | — | — | — | — |

<II. Method>

[II-1. Outline]

In mitochondrial dysfunction, for example, ATP production is damaged and/or oxidative stress increases, with the result that apoptosis of cells is induced. Because of this, individuals having mitochondrial dysfunction are reported to be less tolerant to oxidative stress, compared to normal individuals (Shrader W D et al., Bioorg Med Chem Lett., Jun. 15, 2011, Vol. 21 (12), p. 3693-8, doi: 10.1016/j.bmcl.2011.04.085. electronically published on Apr. 24, 2011, PubMed PMID: 21600768). Then, oxidative stress was given to the skin fibroblasts of individual patients mentioned above to induce apoptosis. Under the conditions, compounds of the drug library were each administered to the cells. In this manner, a primary screening was carried out. Then, candidate pharmaceutical agents selected by the primary screening were subjected to a secondary screening, which is an in-vitro evaluation test such as a mitochondrial function evaluation test and a microarray expression analysis.

[II-2. Oxidative Stress Test]

The oxidative stress test is a known pharmaceutical agent screening method, which was carried out under the conditions where cell death was induced by addition of L-buthionine-(S,R)-sulfoximine (BSO) (Arce P M et al., ACS Med Chem Lett., May 31, 2011, Vol. 2 (8), p. 608-13, doi: 10.1021/m1200095w. eCollection, Aug. 11, 2011, PubMed PMID: 24900356; PubMed Central PMCID: PMC4018135). BSO inhibits synthesis of glutathione serving as an antioxidant in the cells to deplete glutathione, raising the level of active oxygen within the cells. The procedure of the test is as follows. The cells to be used in the test were seeded in a 96-well plate for cell culture so as to satisfy a concentration of 5,000 cells/well and 80 μL medium/well and cultured in a $CO_2$ incubator (37° C., 5% $CO_2$) for 24 hours. Twenty four hours after the culture, BSO and each of the pharmaceutical agents (final concentration of 1 μM) of the drug library were together added to the cells within the wells. Forty eight hours after the addition, survival rates were determined. The survival rates were determined by measuring absorbance of formazan generated by use of cell count reagent SF (Nacalai Tesque, Inc.). As a positive control compound, idebenone (Non Patent Literature 1) approved as a therapeutic agent for Leber's hereditary optic neuritis in Europe, was used in the same concentration.

[II-3. Evaluation Test for Mitochondrial Function]

An evaluation test for mitochondrial function including ATP production (capacity) was carried out by using an extracellular flux analyzer (XFe96, Primetech Corporation). Mitochondrial function can be evaluated by continuously measuring the oxygen consumption rate (OCR) of mitochondria during ATP synthesis by use of the extracellular flux analyzer while adding ATP synthase inhibitors (oligomycin, rotenone and antimycin A) and an uncoupler (carbonyl cyanide-p-trifluoromethoxy phenylhydrazone (FCCP)). The evaluation items to be analyzed were basal respiratory volume, ATP production (capacity) and maximum respiratory volume, which are major indexes for evaluating mitochondrial function. The test procedure is as follows. The cells to be used in the test were seeded in a 96-well plate for cell culture so as to satisfy a concentration of 20,000 cells/well and 80 μL medium/well and cultured in a $CO_2$ incubator (37° C., 5% $CO_2$) for 24 hours. Twenty four hours after the culture, each of the pharmaceutical agents (final concentration of 1,000, 100 or 10 nM) of the drug library or the same amount of dimethyl sulfoxide (DMSO) as a control was added to the cells within wells. Twenty minutes after the addition of the pharmaceutical agent, oligomycin (final concentration of 2 μM) was added. Fifty minutes after the addition of the pharmaceutical agent, FCCP (final concentration of 2 μM) was added. Eighty minutes after the addition of the pharmaceutical agent, rotenone and antimycin A (final concentration of 0.5 μM) were sequentially added. The oxygen consumption rate (OCR) was measured with time. Based on the measurement results 24 hours after the addition of the pharmaceutical agents of the drug library, basal respiratory volume, ATP production (capacity) and maximum respiratory volume were evaluated.

[II-4. Microarray Expression Analysis]

Expression analysis by a microarray was carried out by use of SurePrint G3 Human Gene Expression 8×60K v3 of Agilent Technologies, Inc. To KCMC10 cells derived from patients with Leigh syndrome, BSO was added, to prepare a group of patients provided with oxidative stress. To the cells, BSO and each of the candidate pharmaceutical agents selected from the drug library were both added to prepare another group. In this manner, two samples per each group were prepared. RNA was extracted from each of the samples and subjected to expression analysis by a microarray.

<III. Results>

[III-1. Oxidative Stress Test]

Before screening of pharmaceutical agents of the drug library, the less-tolerance of fibroblasts derived from patients with a mitochondrial disease and provided in I-2, against oxidative stress was checked. The relationship between the concentration of BSO added and the survival rate of the cells tested is shown in FIG. 1. In the figure, A shows the results of ME54 cells derived from a patient with Leigh syndrome; whereas, B shows the results of Promo1 cells as normal cells.

As shown in FIG. 1, the survival rate of ME54 cells derived from a patient with Leigh syndrome significantly decreased at a concentration of 50 μM or more of BSO (FIG. 1A). In contrast, in the Promo 1 cells as normal cells, no significant difference was found in survival rates in the concentration range of 1 to 1000 μM of BSO (FIG. 1B). The same results were confirmed in other fibroblasts derived from patients with a mitochondrial disease (results not shown). From the results, it was demonstrated that the fibroblasts derived from patients with a mitochondrial disease are less tolerant to oxidative stress caused by addition of BSO, compared to the normal-cell control. Such a nature of the fibroblasts derived from patients with a mitochondrial disease is already known from the literature by Shrader W B et al. (Shrader W D et al., Bioorg Med Chem Lett., Jun. 15, 2011, Vol. 21 (12), p. 3693-8, doi: 10.1016/j.bmcl.2011.04.085. electronically published on Apr. 24, 2011, PubMed PMID: 21600768).

Figure 2:
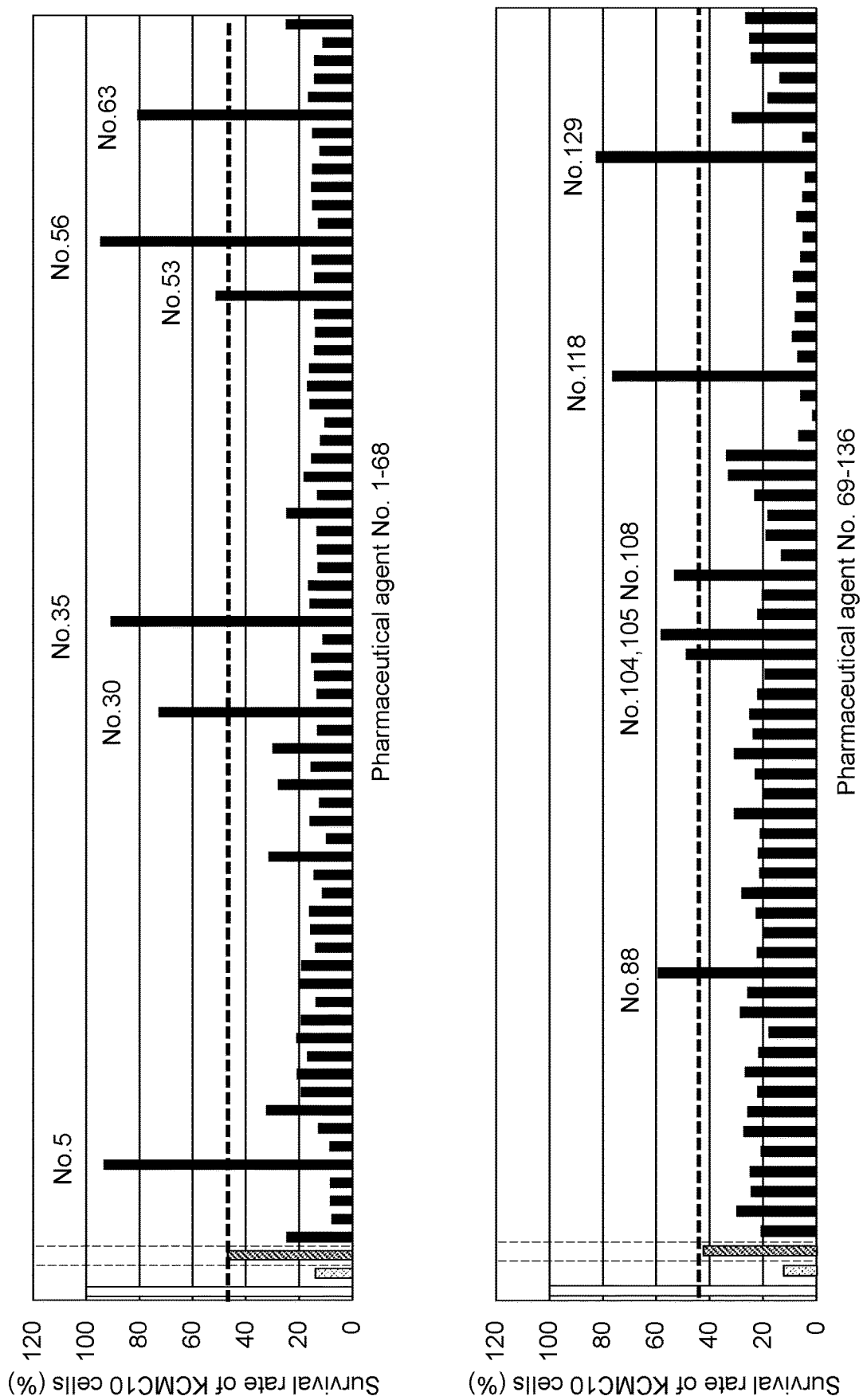
FIG. 2 is a graph showing the results of oxidative stress test of individual pharmaceutical agents of the drug library on KCMC10 cells derived from a patient with Leigh syndrome.
Figure 3:
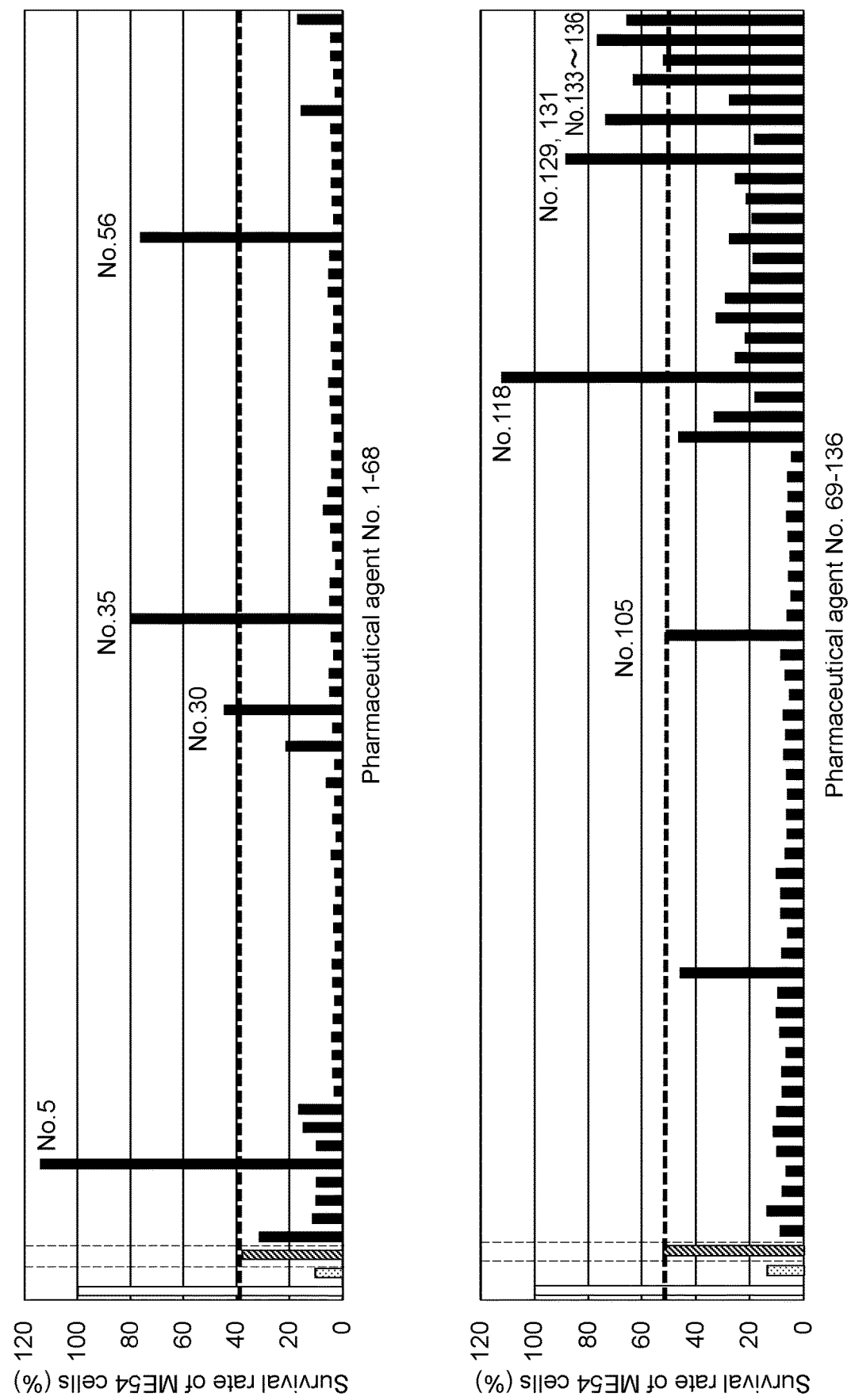
FIG. 3 is a graph showing the results of oxidative stress test of individual pharmaceutical agents of the drug library on ME54 cells derived from a patient with Leigh syndrome.
Figure 4:
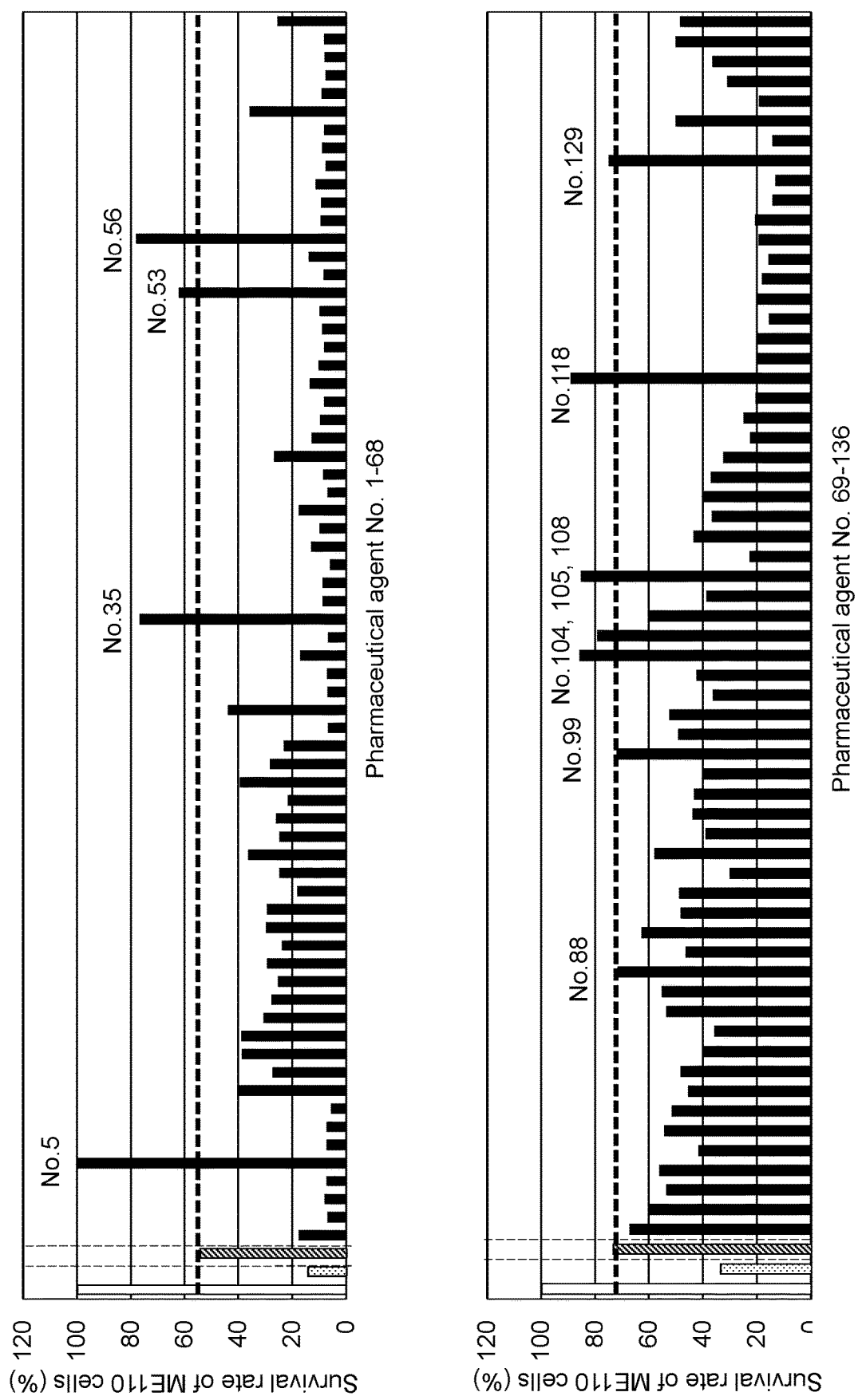
FIG. 4 is a graph showing the results of oxidative stress test of individual pharmaceutical agents of the drug library on ME110 cells derived from a patient with MELAS.

An oxidative stress test was carried out by using three fibroblast cell lines derived from patients with a mitochondrial disease and provided in 1-2. The pharmaceutical agent showing the survival rate equal to or more than that of idebenone, a positive control compound, was determined to be effective. The results of oxidative stress test of pharmaceutical agents of the drug library to KCMC10 cells are shown in FIG. 2; the results of oxidative stress test of pharmaceutical agents of the drug library to ME54 cells are shown in FIG. 3; and the results of oxidative stress test of pharmaceutical agents of the drug library to ME110 cells are shown in FIG. 4. In individual graphs in the figures, the 1st bar from the left (outlined bar) shows a control to which BSO was not added; the 2nd bar (dot pattern) shows a control to which SBO was added and a pharmaceutical agent of the drug library was not added; and the 3rd bar (diagonal pattern) shows a positive control to which SBO and idebenone were added. The horizontal dotted line shows the value of survival rate of a case where idebenone was added determined to be effective.

As shown in FIGS. 2 to 4, 12 types of pharmaceutical agents (pharmaceutical agents No. 5, 30, 35, 53, 56, 63, 88, 104, 105, 108, 118 and 129) were determined to be effective against KCMC10 cells; 12 types of pharmaceutical agents (pharmaceutical agents No. 5, 30, 35, 56, 105, 118, 129, 131, 133, 134, 135 and 136) were determined to be effective against ME54 cells; and 11 types of pharmaceutical agents (pharmaceutical agents No. 5, 35, 53, 56, 88, 99, 104, 105, 108, 118 and 129) were determined to be effective against ME110 cells.

From the above results, six types of pharmaceutical agents (pharmaceutical agents No. 5, 35, 56, 105, 118 and 129), which were determined to be effective against all of the three fibroblast lines derived from patients with a mitochondrial disease, were selected as candidate pharmaceutical agents to be subjected to the secondary screening. The compound names and chemical structures of six types of candidate pharmaceutical agents are shown below.

TABLE 2

| Pharmaceutical agent No. | Compound name | Chemical formula |
| --- | --- | --- |
| 5 | R(−)-Apomorphine hydrochloride hemihydrate | (I-1-1) |
| 35 | Prochlorperazine dimaleate | (I-4-1) |
| 56 | Promazine hydrochloride | (I-5-1) |
| 105 | Asenapine maleate | (I-2-1) |
| 118 | Olanzapine | (I-3-1) |
| 129 | Phenothiazine | (I-6-1) |

[Formula 6]

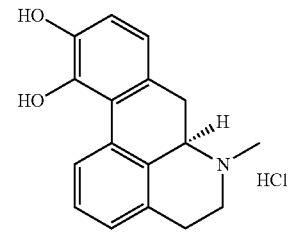

I-1-1

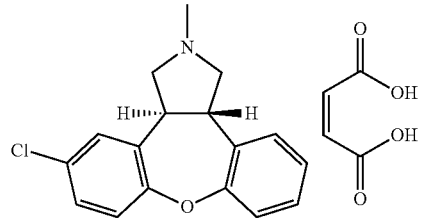

I-2-1

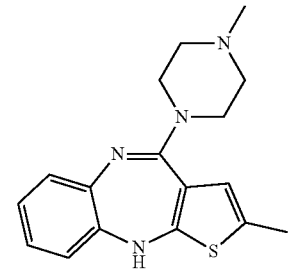

I-3-1

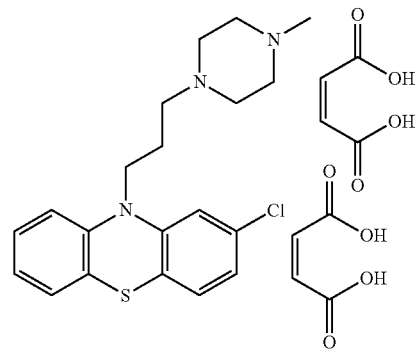

I-4-1

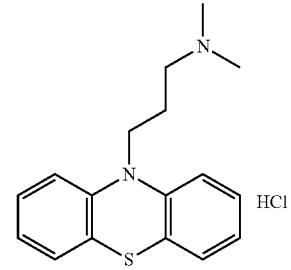

I-5-1

I-6-1

[III-2. Evaluation Test for Mitochondrial Function]

Figure 5:
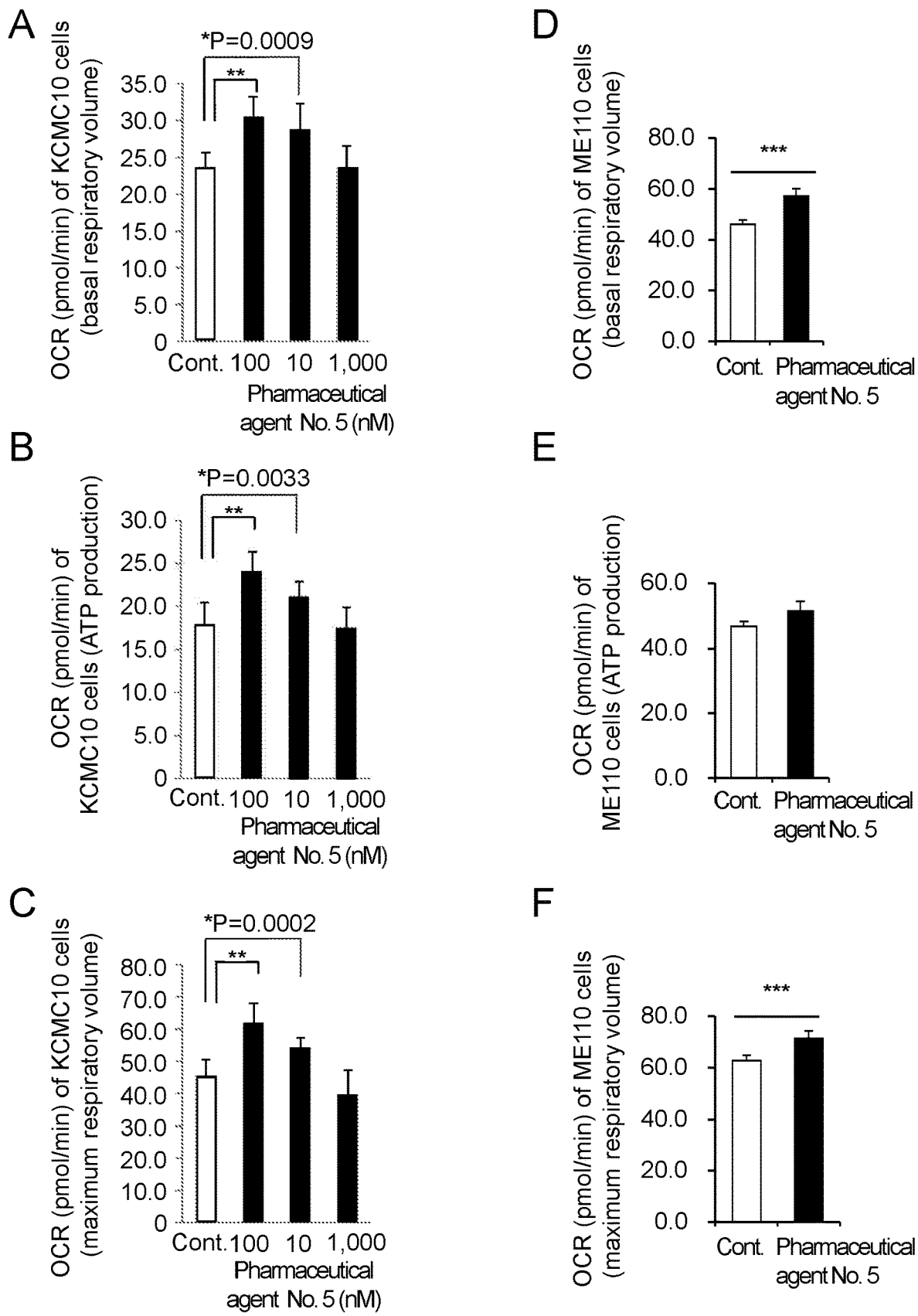
FIG. 5 is a graph showing the evaluation results of basal respiratory volume, ATP production (capacity) and maximum respiratory volume in KCMC10 or ME110 cells 24 hours after the addition of pharmaceutical agent No. 5 (compound of formula (I-1-1)). A: basal respiratory volume in KCMC10 cells, B: ATP production (capacity) in KCMC10 cells, C: maximum respiratory volume in KCMC10 cells, D: basal respiratory volume in ME110 cells, E: ATP production (capacity) in ME110 cells, and F: maximum respiratory volume in ME110 cells.

The evaluation results of basal respiratory volume, ATP production (capacity) and maximum respiratory volume in KCMC10 or ME110 cells 24 hours after the addition of pharmaceutical agent No. 5 (compound of formula (I-1-1)) are shown in FIG. 5. In the figure, A shows the basal respiratory volume in the case where 10, 100 or 1,000 nM pharmaceutical agent No. 5 was added to KCMC10 cells; B shows the ATP production (capacity) in the case where 10, 100 or 1,000 nM pharmaceutical agent No. 5 was added to KCMC10 cells; C shows the maximum respiratory volume in the case where 10, 100 or 1,000 nM pharmaceutical agent No. 5 was added to KCMC10 cells; D shows the basal respiratory volume in the case where 10 nM pharmaceutical agent No. 5 was added to ME110 cells; E shows the ATP production (capacity) in the case where 10 nM pharmaceutical agent No. 5 was added to ME110 cells; and F shows the maximum respiratory volume in the case where 10 nM pharmaceutical agent No. 5 was added to ME110 cells. In the figure, an outlined bar shows the value of a control; whereas a solid bar shows the value of the case where pharmaceutical agent No. 5 was added. Reference symbols of  and *, which represent p values relative to the control (DMSO) calculated by Student's t-test, show less than 0.0001 and less than 0.05, respectively.

As shown in FIG. 5, the basal respiratory volume, ATP production (capacity) and maximum respiratory volume were significantly improved by addition of pharmaceutical agent No. 5 in both KCMC10 and ME110 cells, compared to the control. Particularly, in KCMC10 cells, the basal respiratory volume, ATP production (capacity) and maximum respiratory volume were significantly improved by the addition of pharmaceutical agent No. 5 within the range of 10 to 100 nM, compared to the control. From the above results, it was demonstrated that mitochondrial function can be improved by addition of pharmaceutical agent No. 5 to the skin fibroblasts derived from a patient with a mitochondrial disease, Leigh syndrome or MELAS.

[III-3. Microarray Expression Analysis]

Figure 6:
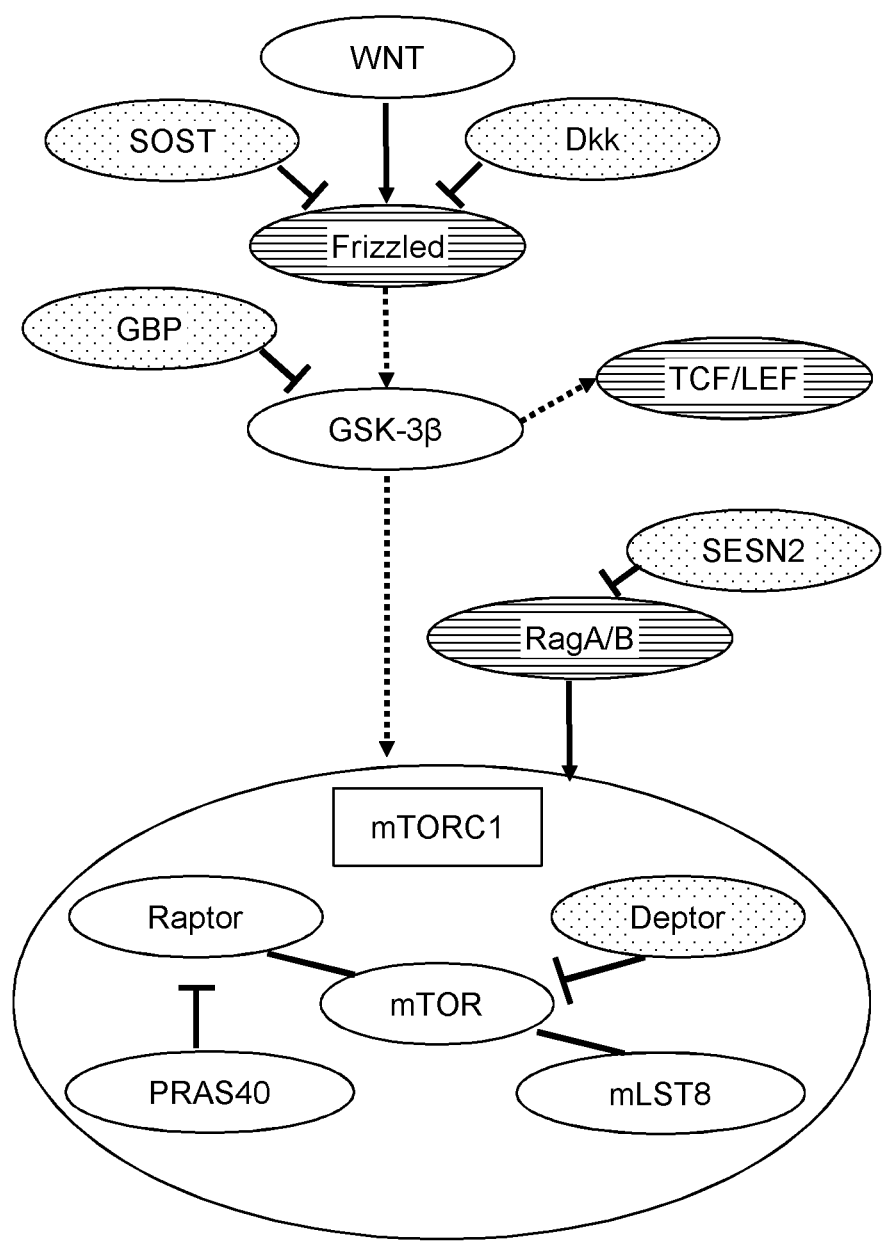
FIG. 6 is a schematic diagram showing the signal pathway in which the genes shown in Table 3 are involved.
Figure 7:
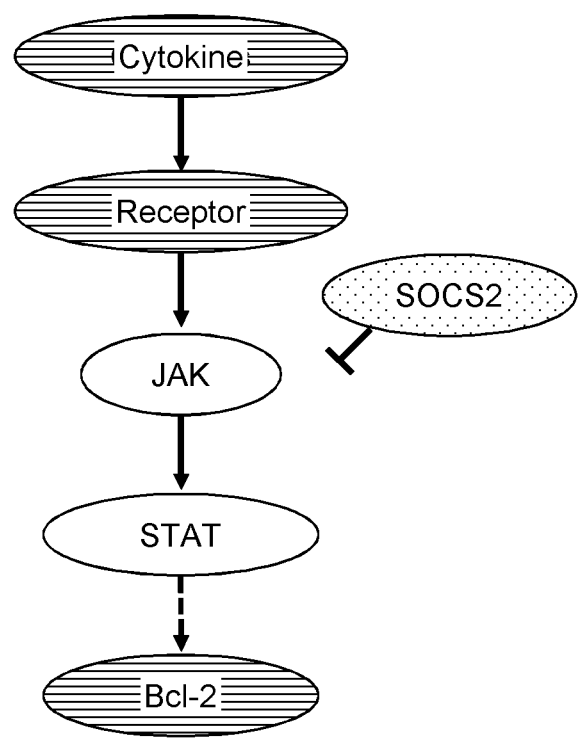
FIG. 7 is a schematic diagram showing the signal pathway in which the genes shown in Table 5 are involved.

Based on comparison of expression-ratio data between the BSO addition group and BSO/pharmaceutical agent No. 5 (compound of formula (I-1-1)) addition group, a gene whose expression ratio differs twice or more between the two groups was determined as a gene showing a significant change in expression by addition of pharmaceutical agent No. 5 and extracted. As a result, 475 types of genes were confirmed as the gene showing a significant change in expression. Information on the genes showing a significant change in expression by addition of pharmaceutical agent No. 5 is listed in Tables 3 to 5. In the tables, the value of Log 2 ratio between the two groups of 1 means that expression ratios differ twice, the value of Log 2 ratio of 2 means 4 times difference and the value of Log 2 ratio of 3 means 8 times difference. The signal pathways in which the genes shown in Table 3 are involved, are schematically shown in FIG. 6; and the signal pathways in which the genes shown in Table 5 are involved are schematically shown in FIG. 7. In the figures, the genes shown in the dot-pattern circle represent genes whose expression increases; and the genes shown in the horizontal-line pattern circle represent genes whose expression decreases.

TABLE 3

| Log 2 ratio between two groups | Expression change (Increase/Decrease) | Name of gene | KEGG pathway |
|---|---|---|---|
| −1.23 | Decrease | LEF1 | WNT signal pathway |
| −1.51 | Decrease | FZD8 | |
| 1.66 | Increase | DKK4 | |
| 1.70 | Increase | SOST | |
| 2.11 | Increase | GBP | |
| −1.61 | Decrease | RNF152 | mTOR signal pathway |
| −1.61 | Decrease | FECN | |
| −1.37 | Decrease | CAB39L | |
| −1.22 | Decrease | RPS6KA1 | |
| −2.27 | Decrease | RRAGD | |
| 1.41 | Increase | SESN2 | |
| 2.11 | Increase | DEPTOR | |
| 4.19 | Increase | PRR5 | |

Of the genes showing a significant change in expression by addition of pharmaceutical agent No. 5, the genes shown in Table 3 were all involved in the WNT-mTOR signal pathway. Overall, the expressions of these genes changed toward suppressing the WNT-mTOR signal pathway.

TABLE 4

| Log 2 ratio between two groups | Expression change (Increase/Decrease) | Name of gene | KEGG pathway |
|---|---|---|---|
| −5.58 | Decrease | CSF3 | Autoimmune disease |
| −4.34 | Decrease | CXCL8 | Neutrophil mobilization |
| −3.72 | Decrease | CXCL3 | Immune to extracellular |
| −2.68 | Decrease | CXCL2 | disease |
| −2.41 | Decrease | CCL7 | |
| −1.40 | Decrease | MMP1 | |
| −3.32 | Decrease | LIF | Inflammatory cytokine |
| −2.98 | Decrease | CCL3 | |
| −1.77 | Decrease | IL24 | |
| −4.92 | Decrease | CCL19 | Lymphocytic tissue homing receptor |
| −3.25 | Decrease | DUSP6 | MARK signal pathway |
| −2.71 | Decrease | IL12A | Proinflammatory effect |

Of the genes showing a significant change in expression by addition of pharmaceutical agent No. 5, the genes shown in Table 4 all related to cytokines or chemokines involved in inflammation or natural immunity. Overall, the expressions of these genes changed toward suppressing expression of the cytokines or chemokines.

TABLE 5

| Log 2 ratio between two groups | Expression change (Increase/Decrease) | Name of gene | KEGG pathway |
|---|---|---|---|
| −1.21 | Decrease | SOSC1 | JAK-STAT signal pathway |
| −1.63 | Decrease | IL13RA2 | |
| −3.90 | Decrease | BCL2A1 | |
| 1.01 | Increase | FHL1 | |
| 1.30 | Increase | SOCS2 | |

Of the genes showing a significant change in expression by addition of pharmaceutical agent No. 5, the genes shown in Table 5 were all involved in the JAK-STAT signal pathway.

The genes showing a significant change in expression by addition of pharmaceutical agent No. 5 and involved in the WNT-mTOR signal pathway, inflammation or natural immunity and JAK-STAT signal pathway may have a possibility to relate to mitochondrial function. It has been reported that mitochondrial function is improved by suppressing, for example, the mTOR signal pathway in Leigh syndrome model mice (Johnson S C et al., Science, Dec. 20, 2013, Vol. 342 (6165), p. 1524-8). Accordingly, it is presumed that mitochondrial function is improved through expression change of these genes by addition of pharmaceutical agent No. 5.

Note that, the present invention is not limited to the aforementioned Examples and includes various modifications. For example, Examples as mentioned above are specifically described in order for the readers to easily understand the present invention and are not always limited to those having all constitutions described. To part of the constitutions of each of the Examples, other constitutions may be added or the constitutions may be partly deleted and/or replaced with other constitutions.

All publications, patents and patent applications cited in the specification are incorporated herein in their entirety by reference.

The invention claimed is:

1. A method for treating a disease or symptom caused by mitochondrial dysfunction, which is at least one mitochondrial disease selected from the group consisting of Leigh syndrome, and mitochondrial encephalopathy, lactic acidosis and stroke-like episodes (MELAS), comprising administering an effective amount of a compound selected from the group consisting of:

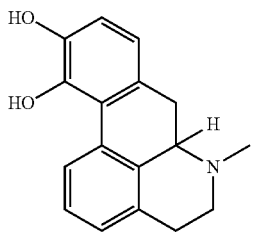

I-1

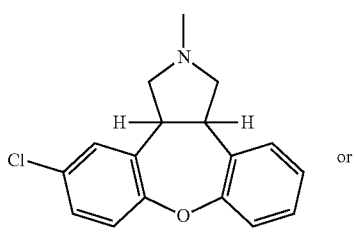

I-2 or

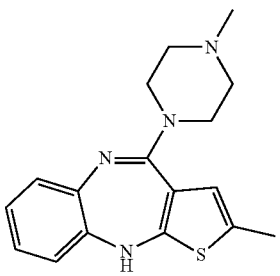

I-3 a stereoisomer or a pharmaceutically acceptable salt thereof, or a pharmaceutically acceptable solvate thereof to a subject requiring treatment of the symptom, disease and/or disorder; and wherein the effective amount of the compound is administered alone as an active ingredient.

2. A method for treating a disease or symptom caused by mitochondrial dysfunction, which is at least one mitochondrial disease selected from the group consisting of Leigh syndrome, and mitochondrial encephalopathy, lactic acidosis and stroke-like episodes (MELAS), comprising administering an effective amount of a compound represented by formula (I-1),

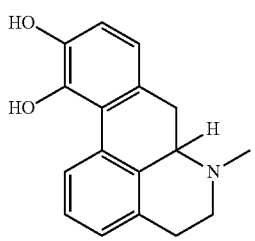

I-1 a stereoisomer or a pharmaceutically acceptable salt thereof, or a pharmaceutically acceptable solvate thereof to a subject requiring treatment of the symptom, disease and/or disorder; and wherein the effective amount of the compound is administered alone as an active ingredient.

3. The method according to claim 1, wherein the disease or symptom caused by mitochondrial dysfunction is Leigh syndrome.

4. The method according to claim 1, wherein the disease or symptom caused by mitochondrial dysfunction is mitochondrial encephalopathy, lactic acidosis and stroke-like episodes (MELAS).

5. The method according to claim 2, wherein the disease or symptom caused by mitochondrial dysfunction is Leigh syndrome.

6. The method according to claim 2, wherein the disease or symptom caused by mitochondrial dysfunction is mitochondrial encephalopathy, lactic acidosis and stroke-like episodes (MELAS).

* * * * *